United States Patent [19]

Simonovitch

[11] Patent Number: 4,792,552

[45] Date of Patent: Dec. 20, 1988

[54] WATER-SOLUBLE ADDUCT OF NORFLOXACIN

[75] Inventor: Haim Simonovitch, L'etzion, Israel

[73] Assignee: Abic Ltd., Israel

[21] Appl. No.: 96,398

[22] Filed: Sep. 11, 1987

[30] Foreign Application Priority Data

Oct. 30, 1986 [IL] Israel ......................... 80459

[51] Int. Cl.[4] .................. A61K 31/495; C07D 401/14
[52] U.S. Cl. ...................................... 514/254; 544/363
[58] Field of Search ......................... 544/363; 514/254

[56] References Cited

U.S. PATENT DOCUMENTS

| | | | |
|---|---|---|---|
| 4,146,719 | 3/1979 | Irikura | 544/363 |
| 4,292,317 | 9/1981 | Pesson | 544/363 |
| 4,352,803 | 10/1982 | Matsumoto et al. | 544/363 |
| 4,522,819 | 6/1985 | Fox et al. | 544/363 |
| 4,670,440 | 6/1987 | Szüts et al. | 544/363 |

*Primary Examiner*—Glennon H. Hollrah
*Assistant Examiner*—James H. Turnipseed
*Attorney, Agent, or Firm*—Steinberg & Raskin

[57] ABSTRACT

The present invention relates to an adduct of nicotinic acid with 1-ethyl-6-fluoro-1,4-dihydro-4-oxo-7-(1-piperazinyl)-3-quinolinecarboxylic acid (Norfloxacin) in particular in a ratio of 1:1. The invention relates also to pharmaceutical compositions and to aqeuous solutions comprising said adduct.

7 Claims, No Drawings

WATER-SOLUBLE ADDUCT OF NORFLOXACIN

BACKGROUND OF THE INVENTION

The present invention relates to a water soluble adduct (as herein defined) of 1-ethyl-6-fluoro-1,4-dihydro-4-oxo-7-(1-piperazinyl)-3-quinolinecarboxylic acid (hereinafter called "Norfloxacin").

Adduct in connection with the present invention means an adduct proper, a salt (including addition salt), a complex etc.

Norfloxacin, which is described and claimed in U.S. Pat. Nos. 4,146,719 and 4,292,314, is a very effective antibacterial agent having a broad spectrum of activity. However, it has a very low water solubility at the normally used pH range, i.e. 6–10.

In many cases it is advantageous to apply a medicament by way of injections, solutions, infusions, etc. Moreover, it is well known that when livestock or fowl are ill the medicament is advantageously administered in the drinking water. As the result of its low water solubility the use of Norfloxacin in the above indicated manner is rather restricted or even impossible.

Certain Norfloxacin salts are known, inter alia, from the following publications:

U.S. Pat. No. 4,530,928 describes and claims a complex of Norfloxacin with guanidium carbonate. However, the solubility of said complex in water is also rather low.

Israeli Pat. No. 66,026 describes and claims the galacturonic, aspartic, glutamic and gluconic salts of Norfloxacin. The solubility of said salts in water is much better. However the preparation of said salts is by way of lyophilization and is expensive.

The above Israeli patent also describes other salts of Norfloxacin. However, it is explicitly stated that these other salts cannot be used for parenteral purposes, i.e. some of them are not sufficiently water-soluble in the required pH range; some are difficult to manufacture by lyophilization (acetate) or the acid part cannot be consistently obtained in a satisfactory grade (lactate).

From DE Pat. No. 3,333,719, a water-soluble composition comprising the lactate of Norfloxacin together with a further acid which does not cause any precipitation is known. This composition is also not satisfactory, not only for the reasons given above, but also because it requires the use of a further acid which complicates the preparation thereof.

It has thus been desirable to find a water-soluble Norfloxacin derivative which overcomes the above drawbacks. Said derivative should, inter alia, be suitable in the veterinary field, e.g. in the treatment of fowl. It should be relatively inexpensive and easy to manufacture, be biostable on being dissolved in water and have a high solubility so that a commercially feasible water concentration can be prepared which can be, if desired, further diluted. Moreover, said derivative should, after having been administered internally, ensure an adequate blood level.

Adducts of nicotinic acid with related acids, e.g. that of Enoxacin and of Pefloxacin were prepared. However, these adducts have a very low solubility in water.

SUMMARY OF THE INVENTION

It has thus been surprising that the nicotinic acid-Norfloxacin adduct (as herein defined), in particular the 1:1 adduct, overcomes the above drawbacks.

Said adduct, while retaining the broad spectrum of activity of Norfloxacin is satisfactorily water-soluble and achieves, after oral administration, adequate blood levels. Moreover, it has a low toxicity. Said adduct has the additional advantage that it uses nicotinic acid which is rather cheap and is known to be a naturally occurring vitamin.

The adduct of the present invention can be administered in a wide variety of therapeutic dosage forms, e.g. by oral administration in the form of tablets or capsules, dissolved in drinking water, as syrup, by intramuscular or intravenous injection or infusion, as ophthalmic solution or ointment, as spray for topical and ear infection, etc.

The adduct according to the present invention is suitably prepared by reacting Norfloxacin with nicotinic acid in a suitable solvent, preferably in boiling ethanol.

The final adduct may be admixed, if desired, with any other suitable compound and/or carrier.

The use of the adduct according to the present invention is illustrated herein with reference to fowl. However, it is not restricted to said use.

DESCRIPTION OF PREFERRED EMBODIMENTS

The present invention will now be illustrated with reference to the Examples without being limited by them.

EXAMPLE 1

10 g of Norfloxacin were added to 20 ml of ethanol, the mixture obtained was then stirred and heated to reflux. 4.2 g of nicotinic acid, previously dissolved in 5 ml of hot ethanol, were added in one portion to said mixture and the resulting suspension was heated to reflux, upon which all solids dissolved. After a short time at reflux the adduct began to separate. The mixture was stirred, cooled to room temperature and finally in an ice bath to yield the nicotinic acid-Norfloxacin 1:1 adduct in 88% yield; m.p. 232°–233° C.

The analysis was calculated for $C_{22}H_{23}FN_4O_5$:

Calculated: C: 59.72%; H: 5.20%; N: 12.66%. Found: C: 59.42%; H: 5.26%; N: 12.70%.

I.R. (KBr cm$^{-1}$): 3075, 3000, 2980, 2960, 1715, 1680 1480, 1350, 1280, 1030, 980, 910, 830, 810, 755, 710, 700, 635,

N.M.R. (D$_2$O):=3.60 (8H.s); 1.5 (3H, t); 4.3 (2H g; 6.84 (1H, d. JFH 7H$_2$); 7.22 (1H, d, JFH 13.5H$_2$); 7.46 (1H, ddd); 8.22 (1H, ddd); 8.44 (1H.5); 8.54 (1H.dd); 8.85 (1H, dd).

M.S. (CI): m/e 320 (protonated Norfloxacin); m/e 124 (protonated nicotinic acid).

LD$_{50}$ (mice oral) > 10 g/kg.

LD$_{50}$ (chicken oral) > 10 g/kg.

The solubility of the adduct at 25° C. in water is 250 mg (equivalent to 180.4 mg Norfloxacin base)/ml.

A solution of 15% in water gives a pH of 5.8.

A solution of 4% in water gives a pH of 6.0.

EXAMPLE 2

The following water-soluble powder was prepared by thorough blending:

30 g of the adduct of Example 1.

6 g sucrose.

6 g ascorbic acid.

EXAMPLE 3

The following water-soluble powder was prepared by thorough blending:
- 30 g of the adduct of Example 1.
- 12 g ascorbic acid.
- 0.39 g nicotinic acid.

EXAMPLE 4

The MIC values are tabulated into Table 1 the columns of which indicate:
- A: Organisms and ATCC code No.
- B: MIC of the compound of Example 1
- C: MIC of cinoxacin
- D: MIC of pipemidic acid
- E: MIC of flumequin
- F: MIC of norfloxacin
- G: MIC of oxalinic acid.

TABLE 1

| No. | A | | B | C | D | E | F | G |
|---|---|---|---|---|---|---|---|---|
| 1 | Enterobacter Cloaca (23355) | | 0.02 | 3 | 0.4 | 0.2 | >0.01 | 0.1 |
| 2 | E. coli 25922 | | 0.02 | 3 | 0.4 | 0.2 | >0.01 | 0.1 |
| 3 | Kleb. Pneumonia (13883) | | 0.05 | 3 | 1.5 | 0.4 | 0.02 | 0.2 |
| 4 | Prot. Vulgaris (13315) | | 0.1 | 3 | 1.5 | 0.2 | 0.01 | 0.1 |
| 5 | Ps. aeruginosa (27853) | | 1.5 | >50 | 50 | 50 | 0.8 | 12 |
| 6 | Sal. typhimuium (14028) | | 0.05 | 6 | 6 | 0.2 | 0.1 | 0.2 |
| 7 | Serratia marcescens (8100) | | 0.05 | 6 | 1.5 | 0.2 | 0.02 | 0.2 |
| 8 | Staff. aureus (25923) | | 1.5 | >50 | 50 | 1.5 | 1.5 | 1.5 |
| 9 | Staph. epidermidis (12778) | | 0.4 | >50 | 6 | 1.5 | 0.2 | 3 |
| 10 | Strep. pyogenes (19165) | | 0.1 | 3 | 3 | 12 | 0.2 | 12 |
| 11 | Strep. faecalis (33186) | | 3 | 50 | 50 | 3 | 3 | 12 |
| 12 | Acinobacter colcoaceticus (19606) | | 6 | 50 | >50 | 0.8 | 6 | 0.8 |
| 13 | Citrobacter-freund (8090) | | 5 | 50 | >50 | 0.2 | 6 | 0.8 |
| 14 | Interobacter aerogenes (13048) | | 0.05 | 6 | 6 | 0.8 | 0.05 | 0.4 |
| 15 | Shigella flexner (12022) | | 6 | 50 | >50 | 0.2 | 6 | 0.8 |
| 16 | Shigella sonnel (25931) | | 3 | 25 | 50 | 0.2 | 3 | 0.4 |
| 17 | Strep. faecalis (19433) | | 3 | >50 | >60 | 25 | 3 | 25 |
| 18 | Strep. agalactiae | | 3 | >50 | >50 | 25 | 3 | 50 |
| 19 | Past. multocida | | 6 | 25 | >50 | 0.2 | 6 | 0.4 |
| 20 | Staph. aureus (25178) | | 0.8 | >50 | 12 | 1.5 | 0.4 | 1.5 |
| 21 | Staph. aureus (8096) | | 0.8 | >50 | 12 | 1.5 | 0.8 | 15 |
| 22 | Past multocida | | >0.01 | 6 | 1.5 | 0.2 | 0.02 | 0.4 |
| 23 | Past multocida | various | 6 | 25 | >50 | 0.2 | 6 | 0.4 |
| 24 | Past multocida | field | 0.02 | 6 | 1.5 | 0.1 | 0.02 | 0.2 |
| 25 | Past multocida | isolates | 0.02 | 1.5 | 1.5 | 0.05 | >0.01 | 0.1 |
| 26 | Past multocida | | 0.02 | 6 | 1.5 | 0.1 | >0.01 | 0.2 |

Comparative Minimal Inhibitory Concentrations (MIC) of several antibacterial quinolones for a wide range of avian pathogenic bacteria a. Stock cultures of the bacteria were maintained on nutrient agar and were sub-cultured periodically to ascertain their viability.

b. Stock solutions, 5 mg/ml, were prepared from each drug. The water soluble drugs were dissolved in sterile distilled water and the water insoluble drugs were dissolved in warm (60° C.) DMSO. The solutions were prepared on the day on which the assay was conducted.

c. The MIC of each drug was determined by the procedure described in Washington, Jr. J. A. & Sutter, B. L. (1980) "Dilution susceptibility test: agar and macro-broth dilution procedures" in *Manual of Clinical Microbiology*, Lennette, E. H. Balows, A. Hauser, W. J. & Truant, J. P., editors, 3rd edith,.pp. 450-453, American Society for Microbiology, Wash. D.C., employing the serial two fold dilution method and Mueller-Hinton agar (Difco) at pH 7.2. Concentrations tested ranged between 50 μg/ml and 0.01 μg/ml. Overnight nutrient broth (Difco) cultures from each bacterial isolate were diluted in 1:100 in sterile saline and approximately 0.01 ml of the diluted culture was placed on the surface of the agar using a modified Steers inoculation device. The bacterial inoculum comprised $5 \times 10^4$ to $1 \times 10^5$ organisms. Inoculated agar plates were incubated aerobically at 37° C. for 18 hours. The MIC was recorded from the lowest drug concentration in the agar which, after incubation, upon visual inspection completely inhibited growth.

EXAMPLE 5

5-week-old Israel commercial strain chickens, heavy breed, were kept for one week before the experiment on feed and water, free of additives and antimicrobial agents, ad lib.

The chicken were randomly divided into three groups of 30 each. The tested compounds were administered continuously in the drinking water at levels at 125 mg/ml of Norfloxacin base.

The medicated water was replaced every 24 hours for group A and B and every 9 hours for group C. (See below). Blood was drawn at $l_0$ (before medication), 12 hours ($t_{12}$), 24 hours ($t_{24}$) and 48 hours ($t_{48}$). Fluorescent lights were kept on throughout the experiment. Temperature monitoring and recording daily: max. 24° C., min. 15° C. The antimicrobial level in the serum for the individual chickens was determined by bioassay PLC determination of Norfloxacin in the serum was performed for the pooled serum in each group. Statistical analysis references: L. A. Gladstone, "Understanding Medican Statistics", William Heinemann Medical Books Ltd., London 1985.

The groups received the following compounds:

Group A 173 mg/ml Norfloxacin nicotinate 1:1 adduct.

Group B 170 mg/ml Norfloxacin methane sulfonate monohydrate.

Group C 125 mg/ml Norfloxavin (by appropriate water dissolution of a composition containing 2.5 g of Norfloxacin, 45.5 ml of propylene glycol and 2 ml of monoethanol amine).

The results for group A are summarized in Table 11.

Group B:

$t_0 = 0$ $t_{12}$ and $t_{24}$ in most birds no detection of serum levels. 14% of birds and serum levels at the range of 0.2 ug/ml serum.

HPLC on pooled serum 0.15 ug/ml serum ±10%.

TABLE 11

Group A $t_0, t_{12}, t_{24}, t_{48}$ hours post mediciation - serum levels of Norfloxacin nicotinate (NORM) in ug/ml serum. Dosage: 125 mg active ingredient/liter drinking water.

| Group | Bird # | $t_0$ | $t_{12}$ | $t_{24}$ | $t_{48}$ |
|---|---|---|---|---|---|
| A | 1 | 0 | 0.12 | 0.24 | 0.20 |
| NORN | 2 | 0 | 0.13 | 0.36 | 0.20 |
|  | 3 | 0 | 0.13 | 0.24 | 0.25 |
|  | 4 | 0 | 0.22 | 0.28 | 0.27 |
|  | 5 | 0 | 0.23 | 0.25 | 0.27 |
|  | 6 | 0 | 0.23 | 0.30 | 0.27 |
|  | 7 | 0 | 0.25 | 0.26 | 0.28 |
|  | 8 | 0 | 0.26 | 0.25 | 0.20 |
|  | 9 | 0 | 0.26 | 0.26 | 0.40 |
|  | 10 | 0 | 0.27 | 0.24 | 0.27 |
|  | 11 | 0 | 0.27 | 0.28 | 0.31 |
|  | 12 | 0 | 0.28 | 0.28 | 0.32 |
|  | 13 | 0 | 0.29 | 0.23 | 0.32 |
|  | 14 | 0 | 0.30 | 0.23 | 0.25 |
|  | 15 | 0 | 0.32 | 0.47 | 0.32 |
|  | 16 | 0 | 0.32 | 0.26 | 0.27 |
|  | 17 | 0 | 0.33 | 0.26 | 0.42 |
|  | 18 | 0 | 0.33 | 0.26 | 0.28 |
|  | 19 | 0 | 0.36 | 0.28 | 0.38 |
|  | 20 | 0 | 0.39 | 0.28 | 0.37 |
|  | 21 | 0 | 0.40 | 0.28 | 0.20 |
|  | 22 | 0 | 0.43 | 0.26 | 0.20 |
|  | 23 | 0 | 0.43 | 0.23 | 0.27 |
|  | 24 | 0 | 0.45 | 0.24 | 0.25 |
|  | 25 | 0 | 0.48 | 0.32 | 0.32 |
|  | 26 | 0 | 0.48 | 0.23 | 0.30 |
|  | 27 | 0 | 0.53 | 0.24 | 0.33 |
|  | 28 | 0 | 0.58 | 0.26 | 0.27 |
|  | 29 | 0 | 0.59 | 0.26 | 0.25 |
|  | 30 | 0 | 0.70 | 0.23 | 0.27 |
| X |  | 0 | 0.35 | 0.27 | 0.28 |
| S.D. |  | 0 | 0.14 | 0.047 | 0.057 |
| S.E. |  | 0 | 0.026 | 0.0086 | 0.010 |
| % response |  | 0 | 100% | 100% | 100% |
| pooled serum bioassay |  | 0 | MD | 0.28 | 0.3 |
| pooled serum HPLC |  | 0 | 0.3,10% | 0.4–10% | 0.4–10% |

Comments:
(1) S.C.-S.D.
(2) √N = 5.48
(3) S.E.-Standard error of the mean √N
(4) 0 = less than our detection level
(5) S.U. - Standard deviation.
(6) N = number of birds/group
(7) N.D. = Not determined.

EXAMPLE 6

Preventive effect of the compound prepared in Example 1 against experimental systemic infection with E. coli 078 in chicken Infection was induced by intraperitoneal injection of 0.5. McF units per kg body weight of E. coli 0.78 suspended in sterile 5% hog stomach mucin in 0.9% saline.

Prior to the experiment the chickens (male, heavy breed 3 weeks old, weighing each 360-700 g) were randomly divided into groups of 30-31, each bird was weighed individually in order to determine the exact inoculum. The chickens were acclimatized for one week before the infection process started and were kept on an antibiotic free diet. Water was supplied ad lib.

The medicament was dissolved in the drinking water reservoirs and was replaced daily. The dosage in all groups was adjusted to a level of 173 mg (125 mg Norfloxacin base) of the compound of example 1 per 1 liter of water.

The medicament was administered immediately post infection induction. The treatment lasted for 3 days, after which the water reservoirs were emptied and refilled with tap water.

Death was recorded daily. 6 days after the infection induction the trial was terminated. The results were summarized in Table III in which:

A stands for control infected, non treated N=31
B stands for a compound of Example 2, N=31
C stands for a compound of Example 1, N=30
D stands for a compound of Example 3, N=30

| Date | A | B | C | D |
|---|---|---|---|---|
| 24.6.86 | starting of the trial | | | |
| 25.6.88 | 6 | 2 | 0 | 2 |
| 26.6.86 | 3 | 0 | 0 | 1 |
| 27.6.86 | 1 | 0 | 0 | 0 |
| 28.6.86 | 3 | 0 | 0 | 0 |
| 29.6.86 | 2 | 0 | 0 | 0 |
| Total Dead | 15 | 2 | 0 | 3 |
| % dead | 48 | 6 | 0 | 10 |

The table clearly proves that the compound prepared by example 1 either by itself or in a formulation effectively protects chickens from E. coli infection.

At the termination of the trial five surviving chickens from each group were euthanised and post mortem examinations were performed. Swabs from peritoneal cavity were taken and immediately applied over EMB agar. No E. coli 078 was found in the peritoneum of the treated (groups B-D) birds. In the infected non-treated control (group A) E. coli was isolated.

I claim:
1. Nicotinic acid:Norfloxacin adduct.
2. Nicotinic acid:Norfloxacin 1:1 adduct.
3. A pharmaceutical composition comprising as active compound an adduct according to claim 1 and a pharmaceutically acceptable carrier.
4. A pharmaceutical composition according to claim 3 being dissolved in water.
5. An aqueous solution comprising an adduct according to claim 1.
6. A method for the treatment of bacterial infections which comprised the administration of a therapeutice effective amount of an adduct according to claim 1.
7. A method according to claim 6, wherein said adduct is dissolved in water.

* * * * *